United States Patent [19]

Bok et al.

[11] Patent Number: 5,273,749
[45] Date of Patent: Dec. 28, 1993

[54] PROCESS FOR PREPARING COATED MICROBIAL PESTICIDES AND PESTICIDES PRODUCED THEREFROM

[75] Inventors: Song H. Bok; Hang W. Lee; Kwang H. Son; Sung U. Kim; Jee W. Lee; Do Y. Kim; Yong K. Kwon, all of Daejeon, Rep. of Korea

[73] Assignee: Korea Research Institute of Chemical Technology, Rep. of Korea

[21] Appl. No.: 838,476

[22] Filed: Feb. 19, 1992

Related U.S. Application Data

[63] Continuation-in-part of Ser. No. 744,260, Aug. 13, 1991, abandoned.

[30] Foreign Application Priority Data

May 23, 1991 [KR] Rep. of Korea .................. 91-8328

[51] Int. Cl.$^5$ .................. A01N 25/26; A01N 63/00
[52] U.S. Cl. .................. 424/405; 424/407; 424/409; 424/410; 424/418
[58] Field of Search .................. 424/405, 408, 409, 488, 424/493, 494, 499, 407, 410, 418–420, 500, 502, 491–492, 93

[56] References Cited

U.S. PATENT DOCUMENTS

| 4,259,317 | 3/1981 | Vesely et al. | 424/93 |
| 4,400,391 | 8/1983 | Connick | 424/304 |
| 4,401,456 | 8/1983 | Connick | 71/88 |
| 4,489,161 | 12/1984 | Papavizas | 435/254 |
| 4,647,537 | 3/1987 | Shigemitsu | 435/178 |
| 4,668,512 | 5/1987 | Lewis et al. | 424/93 |
| 4,713,342 | 12/1987 | Chet et al. | 435/254 |
| 4,724,147 | 2/1988 | Marois et al. | 424/93 |
| 4,748,021 | 5/1988 | Chet et al. | 429/93 |
| 4,985,251 | 1/1991 | Levy | 424/404 |
| 4,992,275 | 2/1991 | Lush | 424/408 |

FOREIGN PATENT DOCUMENTS 0373837  6/1990  European Pat. Off.
2501229  10/1982  France .................. 435/178
2-91010  3/1990  Japan .

Primary Examiner—Thurman K. Page
Assistant Examiner—Neil Levy
Attorney, Agent, or Firm—Timothy R. Kroboth

[57] ABSTRACT

The present invention provides an improved process for preparing coated microbial pesticides comprising antagonistic microorganisms and natural biopolymer originated from natural sources; and pesticides prepared therefrom.

5 Claims, No Drawings

PROCESS FOR PREPARING COATED MICROBIAL PESTICIDES AND PESTICIDES PRODUCED THEREFROM

CROSS REFERENCE TO RELATED APPLICATION

This application is a continuation-in-part application of U.S. Ser. No. 744,260 filed Aug. 13, 1991 entitled "Immobilized Microbial Pesticide and Process for Preparing Same", now abandoned.

FIELD OF THE INVENTION

The present invention relates to an improved process for preparing coated microbial pesticides and products prepared therefrom; and, more specifically, to a process which comprises coating antagonistic microorganisms onto natural biopolymers which are preprocessed to form a gel or paste.

DESCRIPTION OF THE PRIOR ART

Increasingly, the environmental pollution problem has become the subject of everyone's concern: the land and water pollution caused by excessive use of various chemicals, e.g., chemical pesticides, has especially become a controversial issue due to the serious nature of the health and ecological damages therefrom.

Accordingly, in order to ameliorate the environmental pollution problem caused by the use of toxic chemical substances, studies have been made in search for a viable solution for the biological control of plant pathogens through the use of naturally occurring microorganisms.

Specifically, efforts have been made to develop inexpensive and pollutant-free pesticides employing antagonistic microorganisms. However, owing to their inefficiency and other deficiencies associated with the products, the results have been less satisfactory.

For instance, the invention disclosed by Chet et al. in U.S. Pat. No. 4,748,021 is directed to antifungal compositions containing Trichoderma which is active against Fusarium. In a preferred embodiment of their invention, however, the soil is sterilized, e.g., with methyl bromide before the application of a biocontrol composition containing a new microorganism called T-35. According to their invention, the biological composition comprising food base which simply functions as nutrients, additionally contains a certain chemical adhesive to play its roll. Because of these restrictive requirements, the Chet invention lacks practicability or is of limited use.

Vesely et al. in U.S. Pat. No. 4,259,317 disclose a pulverulent preparation containing, as its active ingredient, a high concentration of *Pythium oligandrum* oosphores to be applied onto sugar beet seeds. The finely powdered preparation disclosed in the Vesely patent adheres to the seed surface. The preparation consists of a dried and ground fermented farinaceous substrate on which *Pythium oligandrum* is bred under conditions favoring the sporulation, particularly in the presence of a liquid nutrient containing calcium chloride while irradiating the fermenting substrate. The need to employ the irradiation process and liquid nutrient, among other things, renders the Vesely invention less viable; and the farinaceous substrate employed simply functions as nutrient.

Levy (U.S. Pat. No. 4,985,251) claims an insecticidal composition comprising at least one superabsorbent solid organic polymer comprising hydrophilic acrylamide or acrylate polymers, and a liquid carrier, e.g., water or oil, which makes it difficult to handle and store the composition. Furthermore, the required use of organic polymers such as acrylamide or acrylate polymers in fact undermines the very purpose of developing a biodegradable pesticide.

Jung et al. (French Pat. No. 2,501,229) offer a process for inclusion of microorganisms in a polymer gel matrix based on a crosslinked polysaccharide by use of a metallic salt, e.g., Fe, Al salts or by synergistic treatment with another polysaccharide. The invention disclosed by Jung et al. also uses an absorbent such as synthetic silica, silicoaluminates and cellulose. Consequently, the Jung process is not only cumbersome but also less economical.

Shigemitsu (U.S. Pat. No. 4,647,537) discloses a method for preparing a pesticide containing living biocontrol microorganisms employing carrageenan; Marois et al. (U.S. Pat. No. 4,724,147) describe a method for preparing pellets containing living biocontrol fungi employing an alginate mixture; and Lewis et al. (U.S. Pat. No. 4,668,512) teach a method for preparing pellets containing living biocontrol fungi, ground wheat bran and alginate. However, the microbial pesticides formulated in accordance with these prior art processes do not provide sufficient adhesiveness to the delivery targets such as plant leaves, blades, stems and crops; and, therefore, they are less effective and uneconomical.

As a result, needs have continued to exist for the development of a pollution-free pesticide prepared by using a simple economical process, which is capable of delivering microbial pesticides to a broad range of control subjets with a high degree of efficiency.

SUMMARY OF THE INVENTION

In accordance with the present invention, it has been discovered that coated microbial pesticides prepared by way of coating antagonistic microorganisms onto natural biopolymers can achieve the desired results of providing pollution-free pesticidal effect against a broad range of plant diseases caused by various harmful insects and microorganisms with the concomitant removal of various deficiencies associated with the prior art biological pesticides.

Specifically, the microbial pesticide of the present invention is capable of effectively delivering its bioactive materials to the control subjects such as harmful insects, plant pathogenic fungi, weeds and the like. Further, said pesticide can be prepared economically in accordance with the present invention.

DETAILED DESCRIPTION OF THE INVENTION

The process for preparing a coated microbial pesticide of the present invention comprises:

processing one or more biopolymer materials selected from the group consisting of microbiologically metabolizable bio-polymer-containing natural substances and microbiologically metabolizable bio-polymers extracted therefrom and derivatives thereof into the form of a gel or paste at an elevated temperature;

cooling said processed biopolymers to a lower temperature;

mixing or coating one or more antagonistic microorganisms onto the gel or paste; and then formulating and drying the microorganism-coated biopolymer.

The term "antagonistic microorganism" as used in the present invention is intended to mean a microorganism which eradicates such control subjects as noxious insects, plant pathogenic fungi or weeds, etc., by way of producing and releasing certain bioactive materials, e.g., antibiotics, which are selectively toxic or destructive against the control subjects; or by decimating the control subjects by providing a suppressive or competitive mechanism.

The "bioactive materials" referred to in the present invention are those materials that function as a pesticide.

The term "pesticide" as used herein is intended to include herbicides, insecticides, algicides, bactericides, fungicides, nematicides and the like.

The term "microorganism" as used in the present invention covers a broad spectrum of microorganisms including Gram-negative and positive bacteria, actinomycetes, fungi, yeasts, protozoa, algae and their spores and so on. Exemplary antagonistic microorganisms which may be employed in the present invention include: plant pathogenic fungus-inhibitory microorganisms such as *Bacillus subtilis* subsp. Krictiensis ATCC 55078 and 55079, *Pseudomonas pyrocinia* ATCC 15958, *Pseudomonas fluorescence* ATCC 27663, *Gliocladium virens* ATCC 52045, *Trichoderma reesei* ATCC 28217, *Trichoderma harzianum* ATCC 52445, *Trichoderma hamatum* ATCC 52198, *Trichoderma viride* ATCC 52440 and *Streptomyces cacaoi* subspecies *asoensis* ATCC 19093; insecticidal microorganisms such as *Bacillus thuringiensis* ATCC 13367, *Beauveria bassiana* ATCC 26851, 48585 and 48023, *Hirsutella thomsonii* ATCC 24874, *Metarhizium flavoviride* ATCC 32969 and *Verticillium lencanii* ATCC 46578; and weed-controlling microorganisms such as *Colletrotrichum gloeosporioides* f. sp. *jussiaeas* ATCC 52634.

The process of the present invention further employs a biopolymer made of one or more "natural polymers" selected from the group consisting of microbiologically metabolizable polymer-containing natural substances and microbiologically metabolizable polymers extracted therefrom and derivatives thereof.

Said biopolymers include: grains such as rice, wheat, corn, barley, bean, Italian millet, Indian millet, Chinese millet and buck wheat; tubers such as potato; tuberous roots such as sweet potato and casaba; starches extracted therefrom; and derivatives thereof; and may further include: agar, gelatin, polygalacturonic acid, chitosan, carboxymethyl cellulose, gelrite, natural wax, natural gum and derivatives thereof.

The biopolymer as described above not only satisfies the conventional requirements for an effective pesticide delivery system, but also provides various additional advantages.

First, said polymer can serve as a source of metabolic nutrients to the antagonistic microorganisms; and, therefore, is conducive to the growth and propagation of said microorganisms and the production of bioactive materials.

Secondly, the delivery of the pesticidal components is achieved through a natural process: that is, the antagonistic microorganisms take on the natural biopolymer and catabolize them, thereby attaining a sustained delivery system of bioactive materials.

Thirdly, the natural biopolymer, if processed to a gel or paste, becomes highly adhesive to the delivery targets; and, therefore, the microbial pesticide carried thereby can be effectively delivered to a variety of delivery targets or environment such as soil, water, plants, etc.

Fourthly, the biopolymers as well as the microorganisms are originated from natural environment; and, therefore, the microbial pesticides employing them are basically pollution-free.

Fifthly, the biopolymers employed are mostly inexpensive natural products which are available in abundance; and, therefore, the microbial pesticides of the invention can be prepared at a low cost.

The antagonistic microorganism should be added or coated onto the pre-processed gel-like biopolymer at least in a propagable amount, but not in an excessive amount lest the polymer fulfill its function. Accordingly, the antagonistic microorganism is employed preferably within the range of about $10^4$ to $10^{14}$ cells, more preferably $10^6$ to $10^9$ cells per gram of fully dried microbial pesticide, depending on the microorganism and the natural polymer employed.

Some of the biopolymer materials may be made into a gel or paste by boiling or steaming them at a temperature between 80° C. and 121° C. for 10 to 60 min and mashed to obtain the gel or paste. Certain other materials can be made into a gel or paste by admixing the materials with water and then heating at a temperature between 80° C. and 121° C.

Said boiling, steaming or heating is preferably carried out at a sterilizing temperature, e.g., 121° C. This eliminates the possibility of growth of contaminants found in natural polymers, and enables the antagonistic microorganisms to have an advantage in colonization.

The heated natural polymers should be cooled to a temperature comfortable to the antagonistic microorganism, preferably within a range between a room temperature and about 60° C.

The cooled gel or paste is then mixed with said one or more antagonistic microorganisms. In this step, the culture broth containing the antagonistic microorganisms or the cells and/or spores per se isolated from said culture may be mixed with the prepared gel or paste. Alternatively, lyophilized cells can be directly mixed with said gel or paste.

The mixture of the antagonistic microorganisms and the natural biopolymer can be formulated into powder, pellets, granules, etc. using a conventional formulating machine; and then air-, heat- or freeze-dried to obtain the desired microbial pesticide.

In a continuous process, the antagonistic microorganisms may be liquid-cultured and the cells and/or spores are isolated; while the processed natural biopolymers may be mixed with the culture waste broth, in order thereby to minimize or avoid any pollution or waste problem, and heated to obtain a gel or pasty matrix. After cooling the gel or pasty matrix, the antagonistic microorganism is coated thereon and the coated matrix is formulated and dried.

The coated microbial pesticide of the present invention may further comprise one or more additives such as: nutrient supplements for promoting the growth and propagation of the microorganism or the production of bioactive materials; and/or a microorganism stabilizer for protecting the microorganism during the immobilizing and/or drying process.

Representative microorganism stabilizers include: glycerol, skim milk, milk, dry milk and animal or plant oil.

The nutrient supplements may include: various carbon and nitrogen sources such as cellulose powder, soy bean meal, cotton seed meal, various animal or plant peptone, milk, skim milk, chitin powder, compost powder, wheat bran, corn extract, yeast extract, molasses, glucose, sucrose, dextrin and corn syrup; trace elements such as iron, manganese, zinc and cobalt; soil; soil extract and other materials which are beneficial for increasing the viability of the microorganism. In addition, other materials which improve the properties of the natural biopolymer may be included in the pesticide.

These additives may be added to the collection of, e.g., microorganism cells and the gel or pasty matrix before or simultaneously with the mixing. However, it is preferable to premix the microorganism and the additives.

The coated microbial pesticide may be directly applied to soil or plant; the coated microbial pesticide, due to its excellent adhesiveness, can be applied to growing plants or their products under storage or during transportation thereof; and also be applied near the roots or cuts for protection against pathogens.

The coated microbial pesticide can further be applied to a water culture. To apply the microbial pesticide to a plant growing in a water culture, a floatable pesticide may be provided by coating a floatable material with the microbial pesticide of the present invention. The present invention may employ various natural floatable materials including: puffed grains; floatable agricultural products such as rice bran, nut shell, barley bran, corn husk, wheat straw, barley straw, rice straw, corn stalk, millet stalk, leaves and blades; and sawdust, etc. In a water culture, the disease usually occurs at the water surface, i.e., at the boundary between the part submerged under water and the part exposed from water. Because the floatable pesticide thus obtained floats above the water surface and adheres to said border line areas of the plant, it is very effective to control said site-specific diseases.

It is also possible to coat seeds with the microbial pesticide of the present invention. The seeds so coated are protected from the pathogens; and, therefore, their germinating efficiencies can be improved.

Further, plant seeds can be coated with such other microbial pesticides of the present invention that facilitate the sprouting of the seeds. Specifically, the seeds further treated with a natural pesticide coated with nitrogen-fixing microorganisms, e.g., Rhizobium sp., will have the benefit of securing nutrients from the latter microorganisms.

In the chain of events that may occur after application of the coated microbial pesticide, e.g., application to the soil or plant→growth and propagation of antagonistic microorganism→production of bioacitve material→pesticidal action, the natural biopolymer further functions as a protector and nutrient for the antagonistic microorganism, and, therefore, promotes the growth and propagation of the microorganism and production of the bioactive material.

The coated microbial pesticide, due to its excellent adhesiveness, may be applied directly to the soil and the plant; and, therefore, its antagonism may continue for a prolonged duration. In addition, since the natural biopolymers as well as the microorgaisms are originated from the natural environment, the pesticides produced therefrom are basically natural and pollution-free. Moreover, because the natural biopolymer is made of very inexpensive materials in accordance with a simple process, the present invention is highly economical.

The following examples are intended to further illustrate the present invention, without limiting the scope of the invention. It will be apparent to those skilled in the art that certain changes and modifications can be made to this invention without departing from the spirit or scope of the invention as it is set forth herein.

EXAMPLE 1

1 l of Erlenmeyer flask was filled with 200 ml of a sterilized medium (tryptone 1%, yeast extract 0.5%, NaCl 1%, glucose 1%, pH 7.0) and 5 ml of seed culture (absorbance at 550 nm, 0.4) of *Bacillus subtilis* subsp. *Krictiensis* ATCC 55079 was inoculated thereon, which was then incubated at 37° C. for about 12 hours with shaking. Thereafter, the cells were harvested using a high-speed centrifuge (8000 rpm, 10 min, Sorvall ™, GS-3 rotor) under sterile a condition.

Each of the natural biopolymers listed in Table 1 was mixed with water; heated at the temperature range of 80° to 121° C. for 10 to 60 min to a gel or pasty state; and then cooled to a room temperature. In this step, carboxymethyl cellulose and salts of polygalacturonic acid were not subjected to the heat treatment because they formed gel without heating.

The gel or paste prepared above was mixed with the microbial cell pellet in a quantity of the cell number indicated in Table 1; and mixed to a homogeneous state. The resulting mixture was formulated as granules (diameter 0.1 to 5 mm) and air-dried to obtain the desired coated microbial pesticide.

The pesticide was dissolved and diluted in distilled water and spread over a potato dextrose agar plate, which was then incubated at 30° C. for 24 hours. The viable cell number in the desired pesticide was counted in terms of the number of colonies formed on the agar plate.

From the cell number counted after and before the coating and drying, the viability (%) of the microorganism was determined according to the following equation and the results are provided in Table 1.

$$\text{Viability (\%)} = \frac{\text{Cell No. after coating and drying}}{\text{Cell No. initially inoculated}} \times 100$$

TABLE 1

Viability of Coated Microbial Pesticides Employing Bacillus sp.

| Natural biopolymer | Cell No. initially added (cell/g) | Cell No. after coating/drying (cell/g) | Viability (%) |
|---|---|---|---|
| Bean | $2 \times 10^{10}$ | $1 \times 10^9$ | 5 |
| Foxtail millet | $2 \times 10^{10}$ | $8 \times 10^6$ | 0.04 |
| Chinese millet | $2 \times 10^{10}$ | $2 \times 10^9$ | 10 |
| Corn starch | $1 \times 10^{10}$ | $1 \times 10^6$ | 0.01 |
| Wheat | $1 \times 10^{10}$ | $5 \times 10^7$ | 0.5 |
| Barley | $2 \times 10^{10}$ | $1 \times 10^7$ | 0.05 |
| Rice | $2 \times 10^{10}$ | $1 \times 10^7$ | 0.05 |
| Potato starch | $1 \times 10^{10}$ | $4 \times 10^6$ | 0.04 |
| Sweet potato starch | $2 \times 10^{10}$ | $1.5 \times 10^8$ | 0.80 |
| CMC[a] | $2 \times 10^{10}$ | $7 \times 10^7$ | 0.4 |
| Polygalacturonic acid | $2 \times 10^{10}$ | $1 \times 10^5$ | 0.0005 |
| Gelatin | $2 \times 10^{10}$ | $1 \times 10^5$ | 0.0005 |

TABLE 1-continued

Viability of Coated Microbial Pesticides Employing Bacillus sp.

| Natural biopolymer | Cell No. initially added (cell/g) | Cell No. after coating/drying (cell/g) | Viability (%) |
|---|---|---|---|
| Agar | $1 \times 10^{10}$ | $1.3 \times 10^{6}$ | 0.01 |
| Arabia gum | $2 \times 10^{10}$ | $7 \times 10^{8}$ | 3.5 |
| Gelrite | $2 \times 10^{10}$ | $2 \times 10^{7}$ | 0.10 |
| Chitosan + CMC[a] (1:1, w/w) | $2 \times 10^{10}$ | $5 \times 10^{8}$ | 2.5 |
| Buck wheat | $2 \times 10^{10}$ | $9 \times 10^{8}$ | 4.5 |
| Casaba | $2 \times 10^{10}$ | $9 \times 10^{8}$ | 4.5 | note)
[a] carboxymethyl cellulose

As shown in Table 1, a sufficient number of Bacillus sp. cells remained viable after the coating and drying process employed in accordance with the present invention.

EXAMPLE 2

Various coated microbial pesticides employing *Pseudomonas fluorescence* ATCC 27663 as an antagonistic microorganism and the materials listed in Table 2 as a natural biopolymer were prepared according to the same method as described in Example 1.

Viable cell number was counted after the coating and drying process and the viability (%) of microorganism in the coated microbial pesticide was determined using the formula given above. The results are shown in Table 2.

TABLE 2

Viability of Coated Microbial Pesticides Employing Pseudomonus sp.

| Natural biopolymer | Cell No. initially added (cell/g) | Cell No. after coating/drying (cell/g) | Viability (%) |
|---|---|---|---|
| Chinese millet | $1 \times 10^{9}$ | $8 \times 10^{6}$ | 0.8 |
| Potato starch | $1 \times 10^{9}$ | $9 \times 10^{6}$ | 0.9 |
| Sweet potato starch | $1 \times 10^{9}$ | $2 \times 10^{8}$ | 20 |
| Casaba | $1 \times 10^{9}$ | $6 \times 10^{8}$ | 60 |

As can be seen from Table 2, a sufficient number of Pseudomonas sp. cells remained viable after the coating and drying.

EXAMPLE 3

The same procedure of Example 1 was repeated in a sterilized YM medium(yeast extract 3 g, malt-extract 3 g, peptone 5 g, glucose 10 g, distilled water 1 l, pH 7.0) by employing 5 ml of *Streptomyces cacaoi* subsp. *asoensis* ATCC 19093(absorbance at 550 nm, 0.4).

The data on the viable cell number and the viability are provided in Table 3.

TABLE 3

Viability of Coated Microbial Pesticides Employing Streptomyces sp.

| Natural biopolymer | Cell No. initially added (cell/g) | Cell No. after coating/drying (cell/g) | Viability (%) |
|---|---|---|---|
| Bean | $6 \times 10^{9}$ | $2.2 \times 10^{7}$ | 0.4 |
| Corn starch | $5 \times 10^{9}$ | $1.2 \times 10^{7}$ | 0.2 |
| Rice | $6 \times 10^{9}$ | $5.8 \times 10^{6}$ | 0.1 |
| Gelrite | $6 \times 10^{9}$ | $1 \times 10^{5}$ | 0.002 |
| Soil | $6 \times 10^{9}$ | $1.4 \times 10^{8}$ | 2.0 |
| Chitosan + CMC (1:1, w/w) | $6 \times 10^{9}$ | $3 \times 10^{8}$ | 5.0 |
| Casaba | $6 \times 10^{9}$ | $1.8 \times 10^{5}$ | 3.0 |

EXAMPLE 4

A coated microbial pesticide was prepared in the same manner as in Example 1, with the exception of employing *Bacillus subtilis* subsp. *Krictiensis* ATCC 55078 as the antagonistic microorganism and a gel mixture made of potato starch, rye powder and agar powder in the ratio of 6:3:1 (w/w) as the natural biopolymer.

The viable cell number in the coated microbial pesticide prepared above was counted after the coating and drying process, and the cell viability (%) was measured. The data is shown in Table 4.

Another coated microbial pesticide was prepared in the same manner as above, with the exception of employing potato starch alone as the natural biopolymer; and its data is compared in Table 4.

Table 4

Viability of Coated Microbial Pesticides Employing a Mixed Natural Biopolymer (Potato Starch + Rye Powder + Agar Powder) and a Single Natural Biopolymer

| Natural biopolymer | Cell No. initially added (cell/g) | Cell No. after coating/drying (cell/g) | Viability (%) |
|---|---|---|---|
| Potato starch + rye + agar powder (6:3:1, w/w) | $2.0 \times 10^{12}$ | $3.3 \times 10^{9}$ | 0.2 |
| Potato starch only | $1.1 \times 10^{10}$ | $4 \times 10^{6}$ | 0.04 |

As can be seen from the results in Table 4, the cell viability employing the mixed gel was much higher than that of having the potato starch alone as the natural biopolymer.

EXAMPLE 5

The effect of a microorganism stabilizer on the viability of microorganisms in the coated microbial pesticide was examined by way of repeating two sets of experiments, one set with and the other without using skim milk, in accordance with the same procedure described in Example 1, employing *Bacillus subtilis* subsp. *Krictiensis* ATCC 55078. Potato starch was used in all of the experiments as the natural biopolymer.

The comparative results are shown in Table 5.

TABLE 5

The Effect of Microorganism Stabilizer on the Viability of Microorganism

| Microorganism | Stabilizer (skim milk) | Cell No. initially added (cell/g) | Cell No. after coating/drying (cell/g) | Viability |
|---|---|---|---|---|
| *Bacillus subtilis* | added | $4.0 \times 10^{14}$ | $2.5 \times 10^{14}$ | 63 |

TABLE 5-continued

| | The Effect of Microorganism Stabilizer on the Viability of Microorganism | | | |
|---|---|---|---|---|
| Microorganism | Stabilizer (skim milk) | Cell No. initially added (cell/g) | Cell No. after coating/drying (cell/g) | Viability |
| subsp. Krictiensis ATCC 55078 | not added | $5.7 \times 10^{10}$ | $3.3 \times 10^6$ | 0.006 |

As can be seen from Table 5, when the microorganism stabilizer was used, the cell viability became higher.

EXAMPLE 6

The effect of nutrient supplements on the viability of microorganisms in the coated microbial pesticide was examined.

Bacillus subtilis subsp. Krictiensis ATCC 55079 was inoculated on a liquid medium(soybean powder 1%, yeast extract 0.5%, sugar 3%, $K_2HPO_4$ 0.05%, $MgSO_4 \cdot 7zH_2O$ 0.05%, pH 7.0), which was incubated at 30° C. for 18 hrs; and the cells were harvested by centrifugation.

To prepared a gel or party matrix, 1,000 g of boiled potato and 500 g of boiled rye were thoroughly mashed and mixed. In one experiment, the resulting mixture was added with 200 g of soybean meal powder, 50 g of skim milk and 15 g of sugar as a nutrient source and further mixed; while in another experiment, no such addition was made.

Thereafter, the matrix obtained above was cooled to a room temperature, mixed with 300 g of wet cells prepared above and then formulated as granules with the diameter of 0.1 to 5 mm. The resulting granules were air-dried at a room temperature to obtain the desired coated microbial pesticide.

The viable cell number in the coated microbial pesticide prepared above was counted, and then the pesticide was stood at 30° C. under a relative humidity of more than 90% for 24 hours. Then, the viable cell number was counted to evaluate the effect of the nutrients on the proliferation of the immobilized microorganism.

In addition, the coated microbial pesticide obtained above was incubated at 30° C. and under a relative humidity more than 90% for 24 hrs, and sterilized. Then, the effect of the nutrients on the production of bioactive material, i.e., antibiotics, was evaluated by measuring the diameter of inhibitory zone on potato-dextrose-agar plates employing Pyricularia oryzae, Rhizoctonia solani, Botrytis cinerea as the respective subject test organisms.

The results are provided in Table 6.

TABLE 6

| | The Effect of Nutrients on the Cell Proliferation and the Production of Bioactive Materials | | | | |
|---|---|---|---|---|---|
| | Cell proliferation | | Production of antibiotics (after 24 hrs) | | |
| Nutrients | At the zero time | After 24 hr incubation | Inhibitory zone (mm) | | |
| | | | $P^a$ | $R^b$ | $B^c$ |
| not added | $4 \times 10^8$ | $5 \times 10^5$ | 10 | 13 | 0 |
| added | $9 \times 10^7$ | $4 \times 10^8$ | 17 | 20 | 19 | note)
$P^a$: Pyricularia oryzae
$R^b$: Rhizoctonia solani
$B^c$: Botrytis cinerea

EXAMPLE 7

The germination rate of seeds treated with a coated microbial pesticide was determined as follows.

1 l of Erlenmeyer flask was filled with 200 ml of a sterilized medium(tryptone 1%, yeast extract 0.5%, NaCl 1%, glucose 1%, pH 7.0) and $1 \times 10^9$ cells/ml of Bacillus subtilis subsp. Krictiensis ATCC 55078 were mixed, which was then incubated at 30° C. for about 18 hrs. Thereafter, the cells were harvested by centrifugation at 8000 rpm for 10 min using Sorvall TM high-speed centrifuge(GS-3 Rotor) and suspended in a 10%(v/v) skim milk solution.

Potato starch was kneaded with water, heated at 100° C. for 30 min to a gel state and then cooled to a room temperature.

The gel thus obtained was mixed with about $10^8$ cells/g of said skim milk solution to a homogeneous state. Then, the mixture was formulated as granules with the diameter of 0.1 to 5 mm, and air-dried at a room temperature to obtain the desired coated microbial pesticide.

100 rice seeds were treated with the coated microbial pesticide prepared above and then were sown on a sterilized nutrient-enriched soil, along with 100 untreated rice seeds; all of which were incubated at the temperature range of 25° to 28° C. for 15 days. Thereafter, the number of germinated seeds was counted, and the germination rate was calculated as a percentage of the germinated seeds to the total number of sown seeds. The results are shown in Table 7.

TABLE 7

| Comparison of Germination Rate between Treated and Untreated Seeds | |
|---|---|
| Germination rate of coated seeds (%) | Germination rate of untreated seeds (%) |
| 91 | 73 |

EXAMPLE 8

The protective effect of the floating-type coated microbial pesticide on the rice blast disease and rice sheath blight was examined as follows.

8 l of a liquid medium(soybean meal 2%, glucose 1%, $MnCl_2 \cdot 4H_2O$ 0.005%, NaCl 0.05%, pH 7.0) was charged to a 15 l fermenter and 200 ml of Bacillus subtilis subsp. Krictiensis ATCC 55079 (absorbance at 550 nm, 0.4) was inoculated thereon, which was then incubated at 30° C. for 48 hrs. Then, the cell pellet was concentrated by centrifugation under a sterilized condition and suspended in 500 ml of a 10% (v/v) sterilized skim milk solution.

7.5 l of the resultant supernatant from which said microorganism cells were isolated was added to 800 g of potato starch, 200 g of Indian millet flour, 200 g of cotton seed meal powder and 15 g of glucose; heated at 100° C. with stirring to a pasty state; and cooled to a room temperature.

The resulting paste was mixed with 500 ml of the solution wherein the cells were suspended to a homogeneous state. Thereafter, this mixture was formulated as granules with the diameter of 0.1 to 5 mm and coated with mashed dry lawn leaves at a room temperature to obtain the desired floating-type coated microbial pesticide.

The viable cell number in the coated microbial pesticide obtained above was determined to be $8 \times 10^{11}$ cells/g.

The above pesticide was subjected to the following experiment intended to measure its preventive efficacy of diseases.

Rice was cultivated in pots with sufficient water supply; and, upon its height growing to a length of about 150 cm, spores of *Pyricularia oryzae* were then inoculated to the leaves of rice plants in order to create rice blast disease. After the floating-type coated microbial pesticide was sprayed on the surface of the water in an amount of about 2 g per pot, each pot was subjected to a saturated humidity condition under the temperature range of about 25° to 27° C.; and, untreated rice plants were also subjected to the same condition as above. After about two weeks, the diseased areas of the rice leaves were measured for both the treated and the untreated groups, using the standard scale defined in Table 8. From the measurement, the protection rate (%) was derived by using the following equation and the results are shown in Table 9.

$$\text{Protection rate (\%)} = \left[1 - \frac{\text{Diseased areas (\%) of the treated group}}{\text{Diseased areas (\%) of the untreated group}}\right] \times 100$$

TABLE 8

A Standard Scale for Disease Rating

| Percent of the diseased leaf area | Disease state |
|---|---|
| 0.0% | No diseased area observed |
| 0.2% | Small diseased areas at old leaves rarely observed |
| 0.5% | Small diseased areas at both old and new leaves rarely observed |
| 1.0% | On an average, one diseased area per two or three leaves observed |
| 2.0% | On an average, one diseased area per one leaf observed |
| 5.0% | Two or three diseased areas per one leaf or overall spread of the diseased areas observed |
| 11.0% | New leaves are curled in a very serious condition |
| 25.0% | Plant bodies are curled |
| 55.0% | Plant bodies are seriously curled or withered, or upper leaves are markedly damaged |
| 100.0% | Plant bodies are completely withered or dead |

TABLE 9

Protective Effect of Coated Microbial Pesticide on the Rice Blast Disease and Rice Sheath Blight

| Disease | Treatment | Diseased area of the leaves or sheaths (%) | Protection rate (%) |
|---|---|---|---|
| Rice blast disease | Treated group | 4.0 | 87 |
| | Control group (untreated group) | 30.0 | 0 |
| Rich sheath blight | Treated group | 1.7 | 81 |
| | Control group (untreated group) | 9.0 | 0 |

EXAMPLE 9

The pesticidal activity of the coated microbial pesticide was compared with that of a commercially available chemical pesticide, i.e., procymidone.

Coated microbial pesticide ($8\times10^{11}$ *Bacillus subtilis* cells viable per 1 g of pesticide) was prepared according to the same procedure as in Example 8.

In order to evaluate the controlling effect of said pesticide on gray mold in strawberries, 50 g of said pesticide was sprayed on a lot(500 cm$\times$60 cm) where strawberries(grade: Hokowase) were cultivated to maturity, two times on a 7-day interival. Then, the attack rate was determined 1 and 2 weeks after the spraying. The attack rate was calculated as a percentage of the number of rotten strawberries over the total number of strawberries. The results are shown in Table 1.

For the sake of comparison, 2.5 g of procymidone was sprayed, then the attack rate was measured in the like manner. The results are summarized in Table 10.

TABLE 10

Comparison of the Attack Rate between Coated Microbial Pesticide and Procymidon

| | Attack rate after 1 week from spraying (%) | Attack rate after 2 weeks from spraying (%) |
|---|---|---|
| Coated microbial pesticide-treated group | 10 | 24 |
| Procymidone-treated group | 13 | 32 |
| Control group (untreated group) | 20 | 61 |

What is claimed is:

1. A process for preparing a microbial pesticide which consists essentially of (a) mixing with water and heating a biopolymer selected from the group consisting of microbiologically metabolizable biopolymer-containing natural substances and microbiologically metabolizable biopolymers extracted therefrom, into the form of a gel or paste at a temperature between 80° C. and 121° C., wherein said biopolymer is one or more substances selected from the group consisting of grains, tubers, tuberous roots and starch extracted therefrom; agar; gelatin, polygalacturonic acid; chitosan; carboxymethyl cellulose; gelrite; and natural wax;

(b) cooling said biopolymer gel or paste to a temperature between a room temperature and 60° C.;

(c) mixing one or more antagonistic microorganisms in an amount ranging from about $10^4$ to $10^{14}$ cells per gram of the pesticide, in biologically pure cultures, selected from the group consisting of *Bacillus subtilis* subsp. *Krictiensis* ATCC 55078 and 55079, Pseudomonas pyrocinia ATCC 15958, Pseudomonas fluorescence ATCC 27663, Gliocladium virens ATCC 52045, Trichoderma reesei ATCC 28217, Trichoderma harzianum ATCC 52445, Trichoderma hamatum ATCC 52198, Trichoderma viride ATCC 52440, Streptomyces cacaoi subsp. asoensis ATCC 19093, Bacillus thuringiensis ATCC 13367, Beauveria bassiana ATCC 26851, 48585 and 48023, Hirsutella thomsonii ATCC 24874, Metarhizium flavoviride ATCC 32969, Verticillium lencanii ATCC 46578 and Collectotrichum gloeosporioides f. sp. jussiaeas ATCC 52634 with said cooled biopolymer gel or paste; and then (d) formulating and drying the microorganism-biopolymer gel or paste mixture; whereby an unfermented microbial pesticide is produced.

2. The process of claim 1, wherein said heating is carried out at a sterilizing temperature.

3. The process of claim 1, which further comprises: adding one or more microoganism stabilizers selected from the group consisting of glycerol, skim milk, milk, dry milk, plant oil and animal oil and/or one or more nutrient supplements selected from the group consisting of soy bean meal, cotton seed meal, animal peptone, plant peptone, milk, skim milk, chitin powder, compost powder, wheat bran, corn extract, yeast extract, molasses, glucose, sucrose, dextrin, corn syrup, iron, manganese, zinc, cobalt, soil and soil extract either between step(b) and step(c) or during step(c) of claim 1.

4. A coated microbial pesticide prepared from the process in accordance with claim 1.

5. A process for preparing a floatable microbial pesticide which comprises (a) mixing with water and heating a biopolymer selected from the group consisting of microbiologically metabolizable biopolymer-containing natural substances and microbiologically metabolizable biopolymers extracted therefrom, into the form of a gel or paste at a temperature between 80° C. and 121° C.;

(b) cooling said biopolymer gel or paste to a temperature between a room temperature and 60° C.;

(c) mixing one or more antagonistic microorganisms in an amount ranging from about $10^4$ to $10^{14}$ cells per gram of the pesticide, in biologically pure cultures, selected from the group consisting of Bacillus subtilis subsp. Krictiensis ATCC 55078 and 55079, Pseudomonas pyrocinia ATCC 15958, Pseudomonas fluorescence ATCC 27663, Gliocladium virens ATCC 52045, Trichoderma reesei ATCC 28217, Trichoderma harzianum ATCC 52445, Trichoderma hamatum ATCC 52198, Trichoderma viride ATCC 52440, Streptomyces cacaoi subsp. asoensis ATCC 19093, Bacillus thuringiensis ATCC 13367, Beauveria bassiana ATCC 26851, 48585 and 48023, Hirsutella thomsonii ATCC 24874, Metarhizium flavoviride ATCC 32969, Verticillium lencanii ATCC 46578 and Collectotrichum gloeosporioides f. sp. jussiaeas ATCC 52634 with said cooled biopolymer gel or paste;

(d) formulating and drying the microorganism-biopolymer gel or paste mixture, to provide a microbial pesticide; and then (e) coating a natural source, floatable material with said microbial pesticide, wherein said natural source, floatable material is selected from the group consisting of puffed grain, rice bran, nut shell, barley bran, corn husk, wheat straw, barley straw, rice straw, corn stalk, millet stalk, leaves, blades and sawdust;

whereby a floatable microbial pesticide is produced.

* * * * *